(12) United States Patent
Takita et al.

(10) Patent No.: US 9,345,670 B2
(45) Date of Patent: *May 24, 2016

(54) PATCH PREPARATION

(71) Applicant: NITTO DENKO CORPORATION, Osaka (JP)

(72) Inventors: Tomohito Takita, Ibaraki (JP); Masahiro Mitsushima, Ibaraki (JP); Hidetoshi Kuroda, Ibaraki (JP); Yuji Saeki, Ibaraki (JP)

(73) Assignee: NITTO DENKO CORPORATION, Osaka (JP)

( * ) Notice: Subject to any disclaimer, the term of this patent is extended or adjusted under 35 U.S.C. 154(b) by 182 days.

This patent is subject to a terminal disclaimer.

(21) Appl. No.: 13/951,697

(22) Filed: Jul. 26, 2013

(65) Prior Publication Data

US 2014/0066865 A1 Mar. 6, 2014

(30) Foreign Application Priority Data

Aug. 31, 2012 (JP) ................................. 2012-191409

(51) Int. Cl.
*A61K 9/70* (2006.01)
*A61F 13/02* (2006.01)

(52) U.S. Cl.
CPC .............. *A61K 9/7061* (2013.01); *A61F 13/023* (2013.01); *A61K 9/7046* (2013.01)

(58) Field of Classification Search
CPC ....................................................... A61K 9/70
See application file for complete search history.

(56) References Cited

U.S. PATENT DOCUMENTS

| | | | |
|---|---|---|---|
| 5,374,429 A | 12/1994 | Kinoshita et al. | |
| 7,914,867 B2 | 3/2011 | Mori et al. | |
| 8,096,417 B2 | 1/2012 | Iwao et al. | |
| 8,758,312 B2 * | 6/2014 | Mitsushima et al. | 604/307 |
| 2003/0044599 A1 * | 3/2003 | Sugii et al. | 428/343 |
| 2004/0202708 A1 * | 10/2004 | Roehrig et al. | 424/449 |
| 2006/0078604 A1 | 4/2006 | Kanios et al. | |
| 2007/0154535 A1 * | 7/2007 | Kawamura | 424/449 |
| 2008/0063825 A1 | 3/2008 | Mori et al. | |

(Continued)

FOREIGN PATENT DOCUMENTS

| | | |
|---|---|---|
| EP | 2145633 | 1/2010 |
| JP | 4-244019 | 9/1992 |
| JP | 5-309128 | 11/1993 |

(Continued)

OTHER PUBLICATIONS

EPO Search report, mail date Nov. 6, 2013.

(Continued)

*Primary Examiner* — Carlos Azpuru
*Assistant Examiner* — Casey Hagopian
(74) *Attorney, Agent, or Firm* — Greenblum & Bernstein, P.L.C.

(57) ABSTRACT

The present invention provides a patch preparation that has an extremely low moisture permeability, has a sufficient ODT effect, is excellent in drug releasability, and has a preferred handleability. The patch preparation of the present invention includes a support; and a pressure-sensitive adhesive layer containing an adherent polymer and a drug on one surface of the support, wherein: the support has a polyester base layer, an inorganic oxide layer, and a polyester nonwoven fabric layer in the stated order; the polyester base layer has a thickness of 1.0 μm to 16 μm; and the pressure-sensitive adhesive layer is laminated on the polyester base layer.

6 Claims, 1 Drawing Sheet

(56) References Cited

U.S. PATENT DOCUMENTS

2009/0166236 A1* 7/2009 Iwao et al. .................. 206/438
2010/0015210 A1 1/2010 Funahashi et al.

FOREIGN PATENT DOCUMENTS

| | | |
|---|---|---|
| JP | 8-245380 | 9/1996 |
| JP | 2007-45917 | 2/2007 |
| JP | 2009-120551 | 6/2009 |
| JP | 2009-160388 | 7/2009 |
| JP | 2009-269821 | 11/2009 |
| WO | 2006/043459 | 4/2006 |

OTHER PUBLICATIONS

Official Action for JP Appl. No. 2012-191409 mailed on Mar. 9, 2016.

* cited by examiner

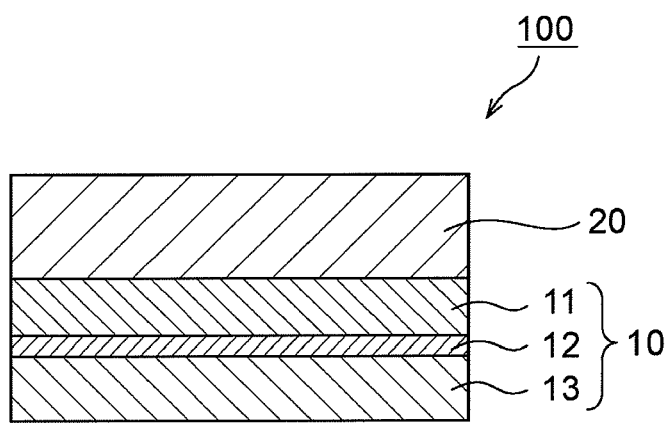

PATCH PREPARATION

This application claims priority under 35 U.S.C. Section 119 to Japanese Patent Application No. 2012-191409 filed on Aug. 31, 2012, which is herein incorporated by reference.

BACKGROUND OF THE INVENTION

1. Field of the Invention

The present invention relates to a patch preparation having a support containing an inorganic oxide layer and a pressure-sensitive adhesive layer containing a drug.

2. Description of the Related Art

In recent years, a transdermal absorption-type patch preparation that delivers a drug into a living organism by being applied to a skin surface has been developed. The patch preparation has been attracting attention because of such an excellent advantage as described below. The patch preparation can maintain a plasma drug concentration within an effective therapeutic range for a long time period, can be easily applied, or can avoid a first liver pass effect. With regard to such patch preparation, the realization of a preparation that exerts a sufficient drug effect with a small preparation area or in a short patch time is expected to lead to an improvement in quality of life (QOL) of a patient. The realization of such preparation requires an improvement in drug releasability. The drug releasability of a patch preparation can be generally improved by such means as the increase of a drug concentration in the patch preparation or the addition of an absorption enhancer. However, such means may adversely affect the physical properties and drug stability of the patch preparation (or its drug-containing pressure-sensitive adhesive layer), and concerns are rising that it takes a considerable time period and a considerable cost to establish means for solving the problem.

A technology for improving the drug releasability by means of an occlusive dressing technique (ODT) effect has been proposed to avoid such problem as described above. Such technology basically involves making the patch preparation lowly moisture-permeable. For example, Japanese Patent Application Laid-open No. Hei 4-244019 describes that drug releasability is improved with the ODT effect caused by covering a support with a covering material that can be easily released and is lowly moisture-permeable. The technology described in Japanese Patent Application Laid-open No. Hei 4-244019 realizes the low moisture permeability not by making the support lowly moisture-permeable but by using the lowly moisture-permeable covering material. In addition, U.S. Patent Application Publication No. 2006-0078604 describes a technology involving causing the ODT effect with a lowly moisture-permeable support to improve drug releasability. The literature describes a single layer or laminate of a specific polymer film as the lowly moisture-permeable support (for example, paragraphs 0369 to 0382).

However, the support itself of the patch preparation described in Japanese Patent Application Laid-open No. Hei 4-244019 is not responsible for the low moisture permeability and hence the following work newly arises: to cover the support with the cover material. In addition, the patch preparation described in U.S. Patent Application Publication No. 2006-0078604 has room for improvement in terms of handleability, though the support itself of the patch preparation is responsible for the low moisture permeability.

SUMMARY OF THE INVENTION

The present invention has been made to solve the conventional problems, and an object of the present invention is to provide a patch preparation that has an extremely low moisture permeability, has a sufficient ODT effect, is excellent in drug releasability, and has a preferred handleability.

The inventors of the present invention have found that the object can be achieved by interposing an extremely thin inorganic oxide layer between a thin polyester base layer and a polyester nonwoven fabric layer in a support of a patch preparation and laminating a pressure-sensitive adhesive layer on the polyester base layer of the support. Thus, the inventors of the present invention have completed the present invention. Further, the inventors of the present invention have found the following. The use of the support of such construction can impart durability to the inorganic oxide layer, and as a result, the inorganic oxide layer can be favorably prevented from dropping off owing to bending or friction, and the flexibility of the patch preparation (and as a result, the patch feeling of the patch preparation) is excellent.

According to the present invention, a patch preparation is provided. The patch preparation includes:

a support; and a pressure-sensitive adhesive layer containing an adherent polymer and a drug on one surface of the support, wherein:

the support has a polyester base layer, an inorganic oxide layer, and a polyester nonwoven fabric layer in the stated order;

the polyester base layer has a thickness of 1.0 µm to 16 µm; and the pressure-sensitive adhesive layer is laminated on the polyester base layer.

In one embodiment of the invention, the inorganic oxide layer has a thickness of 1 nm to 300 nm.

In one embodiment of the invention, the patch preparation has a moisture permeability of 0.1 $g/m^2 \cdot 24$ h to 80 $g/m^2 \cdot 24$ h.

In one embodiment of the invention, the adherent polymer includes an acrylic polymer obtained by copolymerizing a (meth)acrylic acid alkyl ester and a functional monomer.

In one embodiment of the invention, the pressure-sensitive adhesive layer has a thickness of 10 µm to 200 µm.

In one embodiment of the invention, the pressure-sensitive adhesive layer further contains an organic liquid component.

According to the present invention, by interposing an extremely thin inorganic oxide layer between a thin polyester base layer and a polyester nonwoven fabric layer, a patch preparation that has an extremely low moisture permeability, has a sufficient ODT effect, and is excellent in drug releasability can be obtained. Further, the lamination of the pressure-sensitive adhesive layer on the polyester base layer of the support can suppress the moisture permeability of the patch preparation to an extremely low level as compared with the moisture permeability of a patch preparation obtained by laminating the pressure-sensitive adhesive layer on the nonwoven fabric layer of the support, though a mechanism for the foregoing is unknown. As a result, the present invention can realize a patch preparation having extremely high skin permeability of the drug. In addition, the use of the support of such construction can impart durability to the inorganic oxide layer, and as a result, the inorganic oxide layer can be favorably prevented from dropping off owing to bending or friction. Further, the use of the support of such construction provides moderate flexibility, and hence can achieve a high level of compatibility between the handleability and patch feeling of the patch preparation. In addition, the exposed surface of the support of the patch preparation of the present invention is the nonwoven fabric layer. Accordingly, ambient light is diffused and reflected, and hence the patch preparation shows a texture with a mat feeling. In addition, the patch preparation is not conspicuous upon its attachment to a skin even when the patch preparation is not subjected to painting or the like. Accordingly, the patch preparation is excellent in external appearance and eliminates an adverse effect due to paint or the like. Further, the patch preparation of the present invention does not cause any inconvenience even when a user undergoes a checkup such as MRI or CT in a state where the patch preparation is attached to the user.

BRIEF DESCRIPTION OF THE DRAWINGS

FIG. 1 is a schematic sectional view illustrating a patch preparation according to a preferred embodiment of the present invention.

DETAILED DESCRIPTION OF THE PREFERRED EMBODIMENTS

FIG. 1 is a schematic sectional view illustrating a patch preparation according to a preferred embodiment of the present invention. A patch preparation 100 has a support 10 and a pressure-sensitive adhesive layer 20 on one surface of the support 10. The pressure-sensitive adhesive layer 20 contains an adherent polymer and a drug (substantially contains a pressure-sensitive adhesive containing the adherent polymer and the drug). The support 10 has a polyester base layer 11, an inorganic oxide layer 12, and a polyester nonwoven fabric layer 13 in the stated order. Practically, the polyester nonwoven fabric layer 13 is laminated on the inorganic oxide layer 12 through any appropriate adhesive layer (not shown). In the patch preparation 100, the pressure-sensitive adhesive layer 20 is laminated on the polyester base layer 11. Hereinafter, each layer is specifically described.

A. Support

A-1. Polyester Base Layer

The polyester base layer 11 is placed so as to be adjacent to the pressure-sensitive adhesive layer 20. The polyester base layer 11 is constituted of a polyester film. Any appropriate polycondensate of polycarboxylic acid and a polyol can be used as the polyester. Specific examples thereof include polyethylene terephthalate, polybutylene terephthalate, polyethylene naphthalate, polybutylene naphthalate, a copolymer containing repeating units thereof and any other ester repeating units, and a mixture of those polymers and a polymer formed of other ester repeating units. Examples of the polycarboxylic acid component forming the any other ester repeating units include aromatic dicarboxylic acids such as isophthalic acid, diphenyldicarboxylic acid, diphenyletherdicarboxylic acid, diphenylsulfone dicarboxylic acid, and naphthalene dicarboxylic acid; and aliphatic dicarboxylic acids such as adipic acid and sebacic acid. Examples of the polyol component include alkylene glycols such as trimethylene glycol, tetramethylene glycol, and hexamethylene glycol; aromatic diols such as hydroquinone, resorcin, and bisphenol A; aliphatic diols such as bis(hydroxyethoxyphenyl)sulfone and bis(hydroxyethoxyphenyl)propane; and diethylene glycol. Polyethylene terephthalate, a copolymer containing ethylene terephthalate repeating units and any other ester repeating units, and a mixture of polyethylene terephthalate and a polymer formed of any other ester repeating units are preferred. This is because they are superior in safety (nontoxicity) to a living organism, practicality and general-purpose property.

The polyester base layer 11 preferably has as small a thickness as possible. Reducing the thickness can alleviate a stimulus caused by a support edge. Specifically, the thickness is 1.0 µm to 16 µm, preferably 1.0 µm to 12 µm, more preferably 1.0 µm to 10 µm, still more preferably 1.5 µm to 8.0 µm, particularly preferably 2.0 µm to 6.0 µm. When the thickness is less than 1.0 µm, it becomes extremely difficult to handle the layer, which leads to a reduction in yield upon production. When the thickness exceeds 16 µm, the patch preparation may cause a feeling of wrongness (stiff feeling) resulting from the rigidity of the polyester in the case where the patch preparation is attached to a skin surface.

A-2. Inorganic Oxide Layer

In the present invention, the inorganic oxide layer 12 is provided between the polyester base layer 11 and the polyester nonwoven fabric layer 13. Providing such inorganic oxide layer suppresses the moisture permeability of the entire support, and as a result, the moisture permeability of the patch preparation. Thus, the releasability of the drug can be improved by the so-called ODT effect. Further, its inorganic oxide has transparency enough to be used as a base material for the patch preparation, and hence the patch preparation is inconspicuous upon its attachment to a skin. In addition, unlike a metal, the inorganic oxide does not cause any inconvenience even when a user undergoes a checkup such as MRI or CT in a state where the patch preparation is attached to the user.

The inorganic oxide layer 12 is constituted of any appropriate inorganic oxide as long as such effect as described above is obtained. Specific examples thereof include aluminum oxide, silicon oxide, titanium oxide, magnesium oxide, and indium oxide. The inorganic oxides may be used alone or in combination. Of those, aluminum oxide and silicon oxide are preferred. This is because each of those inorganic oxides has particularly high general-purpose property and is excellent in transparency.

The inorganic oxide layer 12 is representatively formed by depositing the inorganic oxide from the vapor onto the polyester base layer. The inorganic oxide layer has a thickness of preferably 1 nm to 300 nm, more preferably 1 nm to 200 nm, still more preferably 1 nm to 100 nm, furthermore preferably 3 nm to 50 nm, still further more preferably 5 nm to 20 nm, particularly preferably 7 nm to 12 nm. In the case where the thickness of the inorganic oxide layer falls within such range, the extent to which the patch preparation is conspicuous at the time of its attachment can be additionally alleviated while its low moisture permeability is maintained. Further, despite the fact that the layer is interposed between the polyester base layer and the polyester nonwoven fabric layer, adhesiveness between those layers can be sufficiently secured.

A-3. Polyester Nonwoven Fabric Layer

The polyester nonwoven fabric layer is constituted of any appropriate polyester nonwoven fabric. Examples of the polyester constituting the nonwoven fabric include the polyesters described in the section A-1 for the polyester base layer. The polyester constituting the nonwoven fabric may be of the same kind as, or of a kind different from, that of the polyester constituting the polyester base layer. The polyester constituting the nonwoven fabric is preferably of the same kind as that of the polyester constituting the polyester base layer. This is because the adhesiveness between the polyester nonwoven fabric layer and the polyester base layer can be made extremely excellent even when the inorganic oxide layer is interposed therebetween. It should be noted that the phrase "polyesters are of the same kind" as used in the specification means that monomers constituting their main repeating units are identical to each other, and the polyesters may be different from each other in copolymerizable component (for example, any other ester repeating unit), or may be different from each other in polymerization degree. The nonwoven fabric can be formed by any appropriate method involving using a polyester fiber. Specific examples of the method of forming the nonwoven fabric include a papermaking method, a hydroentangling method, a needle-punching method, a spun-bonding method, and a melt-blowing method.

The polyester nonwoven fabric has the polyester fibers irregularly placed and hence has stiffness as compared with the thin polyester base layer. Accordingly, providing the polyester nonwoven fabric layer can secure the self-supporting property of the support while maintaining the flexibility of the support. In addition, when the nonwoven fabric layer is placed on a surface opposite to the pressure-sensitive adhesive layer, the nonwoven fabric layer diffuses and reflects ambient light, and hence a texture with a mat feeling arises. Accordingly, the following effect can be obtained: to make an attached site inconspicuous.

The basis weight (weight per unit area) of the polyester nonwoven fabric is not particularly limited. The basis weight of the nonwoven fabric is preferably smaller than the basis weight of a nonwoven fabric to be generally used. With such basis weight, the uncomfortable feeling after the attachment to the skin surface can be alleviated. Specifically, the basis weight of the nonwoven fabric is preferably 5 g/m$^2$ to 25 g/m$^2$, more preferably 5 g/m$^2$ to 20 g/m$^2$, still more preferably 8 g/m$^2$ to 20 g/m$^2$. When the basis weight exceeds 25 g/m$^2$, an uncomfortable feeling may be caused by the nonwoven fabric at the time of the attachment to the skin. When the basis weight is less than 5 g/m$^2$, the inorganic oxide layer cannot be protected from bending, rubbing, or the like, and hence the durability of the inorganic oxide layer becomes poor in some cases.

B. Pressure-Sensitive Adhesive Layer

As described above, in the present invention, the pressure-sensitive adhesive layer 20 is laminated on the polyester base layer of the support. Adopting such construction can suppress the moisture permeability of the patch preparation to an extremely low level as compared with the moisture permeability of a patch preparation obtained by laminating the pressure-sensitive adhesive layer on the nonwoven fabric layer of the support. As a result, the present invention can realize a patch preparation having extremely high skin permeability of the drug. Further, the nonwoven fabric layer as the exposed surface of the support diffuses and reflects ambient light, and hence a patch preparation showing a texture with a mat feeling and having an inconspicuous external appearance can be realized.

The pressure-sensitive adhesive layer 20 contains the pressure-sensitive adhesive containing the adherent polymer and the drug. The pressure-sensitive adhesive to be used in the pressure-sensitive adhesive layer is not particularly limited. Specific examples of the pressure-sensitive adhesive include an acrylic pressure-sensitive adhesive containing an acrylic polymer; a silicone-based pressure-sensitive adhesive such as a silicone rubber, a dimethylsiloxane base, or a diphenylsiloxane base; a rubber-based pressure-sensitive adhesive such as a styrene-diene-styrene block copolymer (such as a styrene-isoprene-styrene block copolymer or a styrene-butadiene-styrene block copolymer), a polyisoprene, a polyisobutylene, or a polybutadiene; a vinyl ether-based pressure-sensitive adhesive such as polyvinyl methyl ether, polyvinyl ethyl ether, or polyvinyl isobutyl ether; a vinyl ester-based pressure-sensitive adhesive such as a vinyl acetate-ethylene copolymer; and a polyester-based pressure-sensitive adhesive formed of a carboxylic acid component such as dimethyl terephthalate, dimethyl isophthalate, or dimethylphthalate and a polyhydric alcohol component such as ethylene glycol. One kind of those pressure-sensitive adhesives may be used alone, or two or more kinds thereof may be used in combination. A nonaqueous pressure-sensitive adhesive layer is preferred from the viewpoint of skin adhesion, and hence a hydrophobic pressure-sensitive adhesive is preferred. The term "nonaqueous pressure-sensitive adhesive layer" as used herein is not strictly limited to one containing no moisture but comprehends a pressure-sensitive adhesive layer containing a slight amount of moisture derived from air humidity, the skin, or the like.

In one embodiment, the pressure-sensitive adhesive layer (substantially the pressure-sensitive adhesive) contains an acrylic polymer as the adherent polymer. According to the present invention, as described above, the moisture permeability can be suppressed with the support in an extremely favorable fashion. Accordingly, a large number of advantages of the acrylic polymer can be effectively exploited while a problem of the acrylic polymer, i.e., its relatively large moisture permeability is solved. The acrylic polymer preferably has adherence at normal temperature (for example, 25° C.). Such acrylic polymer is preferably an acrylic polymer obtained by copolymerizing a (meth)acrylic acid alkyl ester and a functional monomer, and is more preferably an acrylic polymer obtained by copolymerizing the (meth)acrylic acid alkyl ester as a main component with the functional monomer. The term "main component" as used herein means a monomer whose content is 50 wt % or more on the basis of the total weight of all monomers constituting the copolymer.

As the (meth)acrylic acid alkyl ester (which may hereinafter be referred to as "main monomer") in the acrylic polymer, any appropriate (meth)acrylic acid alkyl ester may be used. Representative examples thereof include (meth)acrylic acid alkyl esters, the alkyl group of which is a linear or branched alkyl group having 4 to 13 carbon atoms (for example, butyl, pentyl, hexyl, heptyl, octyl, 2-ethylhexyl, nonyl, decyl, undecyl, dodecyl, or tridecyl). The (meth)acrylic acid alkyl ester may be used alone or in combination of two or more kinds.

The term "functional monomer" as used in the specification means a monomer having at least one unsaturated double bond which is involved in a copolymerization reaction in its molecule, and having a functional group in its side chain. Specific examples of the functional monomer include a carboxylic group-containing monomer such as (meth)acrylic acid, itaconic acid, maleic acid, or maleic acid anhydride; a hydroxyl group-containing monomer such as a (meth)acrylic acid hydroxyethyl ester or a (meth)acrylic acid hydroxypropyl ester; a sulfoxyl group-containing monomer such as styrenesulfonic acid, allylsulfonic acid, sulfopropyl(meth)acrylate, (meth)acryloyloxynaphthalene sulfonic acid, or acrylamide methylpropane sulfonic acid; an amino group-containing monomer such as a (meth)acrylic acid aminoethyl ester, a (meth)acrylic acid dimethylaminoethyl ester, or a (meth)acrylic acid tert-butylaminoethyl ester; an amide group-containing monomer such as (meth)acrylamide, dimethyl(meth)acrylamide, N-methylol (meth)acrylamide, N-methylol propane (meth)acrylamide, or N-vinyl acetamide; and an alkoxyl group-containing monomer such as a (meth)acrylic acid methoxyethyl ester, a (meth)acrylic acid ethoxyethyl ester, a (meth)acrylic acid methoxyethylene glycol ester, a (meth)acrylic acid methoxydiethylene glycol ester, a (meth)acrylic acid methoxypolyethylene glycol ester, a (meth)acrylic acid methoxypolyprene glycol ester, or a (meth)acrylic acid tetrahydrofuryl ester. The functional monomer may be used alone or in combination of two or more kinds. Of those, in view of pressure-sensitive adherence, cohesiveness, or the like of the pressure-sensitive adhesive layer, the carboxy group-containing monomer is preferred, and (meth)acrylic acid is more preferred.

As the acrylic polymer, an acrylic polymer obtained by copolymerizing a main monomer, a functional monomer, and any other monomer may be used. Examples of the any other monomer include (meth)acrylonitrile, vinyl acetate, vinyl propionate, N-vinyl-2-pyrrolidone, methyl vinyl pyrrolidone, vinyl pyridine, vinyl piperidone, vinyl pyrimidine, vinyl piperazine, vinyl pyrrole, vinyl imidazole, vinyl caprolactam, and vinyl oxazole. The any other monomer may be used alone or in combination of two or more kinds.

Examples of the particularly preferred acrylic polymer in the present invention include a copolymer of acrylic acid 2-ethylhexyl ester/acrylic acid, a copolymer of acrylic acid 2-ethylhexyl ester/acrylic acid/N-vinyl-2-pyrrolidone, and a copolymer of acrylic acid 2-ethylhexyl ester/acrylic acid 2-hydroxyethyl ester/vinyl acetate. The copolymer of acrylic acid 2-ethylhexyl ester/acrylic acid and the copolymer of acrylic acid 2-ethylhexyl ester/acrylic acid/N-vinyl-2-pyrrolidone are preferred.

Copolymerization ratios (usage ratios of the monomers) in the acrylic polymer are, for example, as follows: the (meth) acrylic acid alkyl ester (main monomer), the functional monomer, and the any other monomer are used at ratios of 50 wt % to 99.9 wt %, 0.1 wt % to 10 wt %, and 0 wt % to 49.9 wt %, respectively with respect to the total weight of the monomers to be used. Adopting such copolymerization ratios provides an acrylic polymer that has good adhesion to a human skin, and can be repeatedly bonded and released with ease.

The acrylic polymer can be obtained by any appropriate polymerization method. For example, the polymer can be obtained by: adding a polymerization initiator (such as benzoyl peroxide or 2,2'-azobisisobutyronitrile) to the monomers; and causing the contents to react with each other in a solvent (such as ethyl acetate) at 50° C. to 70° C. for 5 hours to 48 hours.

The amount of the adherent polymer (such as the acrylic polymer) in the pressure-sensitive adhesive layer is preferably 30 wt % to 70 wt %, more preferably 40 wt % to 70 wt % on the basis of the total weight of the pressure-sensitive adhesive layer. When the amount of the adherent polymer falls short of 30 wt %, the internal cohesive strength of the pressure-sensitive adhesive layer may reduce. When the amount of the adherent polymer exceeds 70 wt %, the tack of the pressure-sensitive adhesive layer may reduce, or the addition amount of an organic liquid component to be described later may be insufficient.

The drug contained in the pressure-sensitive adhesive layer is not particularly limited. A drug which can be administered to mammals such as humans through their skin, that is to say, a drug capable of transdermal absorption is preferred. Specific examples of such drug include general anesthetics, hypnotics, antiepileptics, antipyretic analgesics, anti-vertigenous drugs, psychoneurotic agents, central nervous system agents, antidementia drugs, local anesthetics, skeletal muscle relaxants, autonomic nervous system agents, spasmolytics, antiparkinson agents, antihistamines, cardiac stimulants, antiarrhythmic agents, diuretics, hypotensive agents, vasoconstrictors, coronary vasodilators, peripheral vasodilators, antiarteriosclerosis agents, cardiovascular preparations, anapnoics, antitussives and expectorants, hormone preparations, dermatics for purulence, analgesics, anti-itchings, astrigents and anti-inflammatory agents, anti-dermoinfectives, hemostatics, gout suppressants, antidiabetic agents, antineoplastics, antibiotics, chemotherapeutics, narcotics, and smoking-cessation aids.

The drug can be present in the pressure-sensitive adhesive layer in an amount enough to provide a desired result, e.g., a desired therapeutic result in the therapy of a disease, a state, or a disability (that is, an effective dose). The term "effective dose of the drug" means, for example, such a sufficient amount of the drug that the drug is nontoxic but exerts a selected effect over a specific time period. Such amount can be easily determined by a person skilled in the art.

The amount of the drug in the pressure-sensitive adhesive layer is not particularly limited as long as its effect as a drug for transdermal absorption is satisfied and the adhesion characteristic of the pressure-sensitive adhesive is not impaired. Specifically, the amount of the drug is preferably 0.1 wt % to 60 wt %, more preferably 0.5 wt % to 40 wt % on the basis of the total weight of the pressure-sensitive adhesive layer. When the amount of the drug is less than 0.1 wt %, its therapeutic effect may be insufficient. When the amount of the drug is more than 60 wt %, the contents of the pressure-sensitive adhesive and any other additive constituting the pressure-sensitive adhesive layer reduce, and hence sufficient skin adhesion may not be obtained. In addition, such amount may be economically disadvantageous.

An organic liquid component can be further incorporated into the pressure-sensitive adhesive layer (substantially the pressure-sensitive adhesive) as required. The use of the organic liquid component enables, for example, the regulation of the adherence and/or the promotion of the transdermal absorption of the drug. Examples of the organic liquid component include glycols such as ethylene glycol, diethylene glycol, triethylene glycol, propylene glycol, polyethylene glycol, and polypropylene glycol; oil and fat such as olive oil, castor oil, squalene, and lanolin; organic solvents such as ethyl acetate, ethyl alcohol, dimethyldecyl sulfoxide, methyloctyl sulfoxide, dimethyl sulfoxide, dimethyl formamide, dimethyl acetamide, dodecyl pyrrolidone, and isosorbitol; liquid surfactants; plasticizers such as diisopropyl adipate, phthalic acid ester, diethyl sebacate, triethyl citrate, and acetyl tributyl citrate; hydrocarbons such as liquid paraffin; and esters such as ethoxylated stearyl alcohol, a glycerin fatty acid ester, and a fatty acid ester. The organic liquid component may be used alone or in combination of two or more kinds.

Preferred examples of the organic liquid component include a fatty acid ester, a glycerin fatty acid ester (especially a mono-, di-, or triglyceride), and acetyl tributyl citrate. Those components each exert an excellent plasticizing action on the pressure-sensitive adhesive layer. With regard to the fatty acid ester and the glycerin fatty acid ester out of those components, a fatty acid ester of a higher fatty acid and a lower monohydric alcohol is preferred from the viewpoints of: maintaining compatibility with the adherent polymer in the pressure-sensitive adhesive layer; and preventing vaporization in a heating step upon preparation of the patch preparation. Examples of the higher fatty acid include fatty acids each having preferably 12 to 16, more preferably 12 to 14 carbon atoms. Specific examples thereof include lauric acid, myristic acid, and palmitic acid. Examples of the lower monohydric alcohol include monohydric alcohols each having 1 to 4 carbon atoms. Specific examples thereof include methanol, ethanol, propanol, isopropanol, and butanol.

The amount of the organic liquid component in the pressure-sensitive adhesive layer (substantially the pressure-sensitive adhesive) is preferably 10 wt % to 70 wt %, more preferably 20 wt % to 60 wt %, still more preferably 30 wt % to 50 wt % on the basis of the total weight of the pressure-sensitive adhesive layer. When the amount of the organic liquid component falls short of 10 wt %, keratin peels upon release of the patch preparation, which may do damage to the skin. When the amount of the organic liquid component exceeds 70 wt %, the adhesion may be insufficient.

The pressure-sensitive adhesive layer (substantially the pressure-sensitive adhesive) may further contain any other component to such an extent that an effect of the present invention is not impaired. Examples of such any other component include an antioxidant such as ascorbic acid, tocopherol acetate, natural vitamin E, dibutylhydroxytoluene, or butylhydroxyanisole, an amine-ketone-based age resister such as 2,6-tert-butyl-4-methylphenol, an aromatic secondary amine-based age resister such as N,N'-di-2-naphtyl-p-phenylenediamine, a monophenol-based age resister such as a 2,2,4-trimethyl-1,2-dihydroquinoline polymer, a bisphenol-based age resister such as 2,2'-methylene bis(4-ethyl-6-tert-butylphenol), a polyphenol-based age resister such as 2,5-tert-butylhydroquione, a filler such as kaolin, hydrated silicon dioxide, zinc oxide, or starch acrylate 1000, a softener such as propylene glycol, a polybutene, or macrogol 1500, a preservative such as benzoic acid, sodium benzoate, chlorhexidine hydrochloride, sorbic acid, methyl paraoxybenzoate, or butyl paraoxybenzoate, a colorant such as yellow iron oxide, yellow ferric oxide, iron sesquioxide, black iron oxide, carbon black, carmine, β-carotene, copper chlorophyll, food blue No. 1, food yellow No. 4, food red No. 2, or a glycyrrhiza extract, a cooling agent such as fennel oil, d-camphor, dl-camphor, peppermint oil, d-borneol, or l-menthol, and a perfume such as spearmint oil, clove oil, vanillin, bergamot oil, or lavender oil. The kind and amount of the any other component to be contained may be appropriately set depending on purposes.

In the present invention, the pressure-sensitive adhesive layer (substantially a pressure-sensitive adhesive layer-forming composition) may be subjected to a physical cross-linking treatment based on, for example, radiation irradiation such as UV light irradiation or electron beam irradiation, or a chemical cross-linking treatment involving using any one of the various cross-linking agents as required.

Any such cross-linking agent is not particularly limited as long as the cross-linking agent is such that the formation of cross-links is not inhibited by the drug. Specific examples of the cross-linking agent include a peroxide (such as benzoyl peroxide (BPO)), a metal oxide (such as magnesium aluminometasilicate), a polyfunctional isocyanate compound, an organic metal compound (such as zirconium and zinc alaninate, zinc acetate, zinc ammonium glycinate, or a titanium compound), a metal alcoholate compound (such as tetraethyltitanate, tetraisopropyl titanate, aluminum isopropylate, or aluminum sec-butylate), and a metal chelate compound (such as titanium dipropoxy bis(acetylacetonate), tetraoctylene glycol titanium, aluminum isopropylate, ethyl acetoacetate aluminum diisopropylate, aluminum tris(ethylacetoacetate), or aluminum tris(acetylacetonate)). The cross-linking agent may be used alone or in combination of two or more kinds. Of those, the polyfunctional isocyanate compound and the metal chelate compound are preferred. This is because those compounds each have high cross-linking efficiency in an acrylic pressure-sensitive adhesive having a carboxyl group.

When the cross-linking agent is used, its usage is preferably 0.01 wt % to 10 wt %, more preferably 0.05 wt % to 5 wt % on the basis of the total weight of the pressure-sensitive adhesive layer. When the usage of the cross-linking agent is less than 0.01 wt %, the number of cross-link points is so small that a sufficient cohesive strength cannot be imparted to the pressure-sensitive adhesive layer, and hence an adhesive residue or a strong skin stimulus resulting from the cohesive failure of the layer may occur at the time of the release. When the usage of the cross-linking agent is more than 10 wt %, the cohesive strength is large but a sufficient skin adhesive strength cannot be obtained in some cases. In addition, a skin stimulus may occur owing to the remaining of an unreacted cross-linking agent.

The chemical cross-linking treatment can be performed through, for example, such a step that after the addition of the cross-linking agent to the pressure-sensitive adhesive layer, the pressure-sensitive adhesive layer is heated to a temperature equal to or more than its cross-linking reaction temperature and then stored, i.e., an aging step. A heating temperature and a heating time are appropriately selected depending on the kind of the cross-linking agent. The heating temperature is preferably 60° C. to 90° C., more preferably 60° C. to 80° C. The heating time is preferably 12 hours to 96 hours, more preferably 24 hours to 72 hours. The cross-linked pressure-sensitive adhesive layer containing the organic liquid component is preferred because the layer shows a gel state, and hence has moderate skin adhesion and has such cohesiveness as to hardly cause an adhesive residue at the time of its release.

The thickness of the pressure-sensitive adhesive layer is preferably 10 μm to 200 μm, more preferably 15 μm to 150 μm from the viewpoint of skin adhesion.

C. Patch Preparation

The patch preparation of the present invention is obtained by forming the pressure-sensitive adhesive layer described in the section B on the surface on the polyester base layer side of the support described in the section A. The patch preparation of the present invention is provided as a transdermal absorption-type preparation, and is provided as a matrix-type patch preparation, a reservoir-type patch preparation, or the like, in particular, as a matrix-type patch preparation.

The moisture permeability of the patch preparation is preferably 0.1 $g/m^2 \cdot 24$ h to 80 $g/m^2 \cdot 24$ h, more preferably 0.5 $g/m^2 \cdot 24$ h to 70 $g/m^2 \cdot 24$ h, still more preferably 1 $g/m^2 \cdot 24$ h to 60 $g/m^2 \cdot 24$ h. As long as the moisture permeability of the patch preparation falls within such range, a sufficient ODT effect is obtained and the releasability of the drug can be improved. According to the present invention, such extremely low moisture permeability can be realized while the transparency of the entire patch preparation is maintained. The moisture permeability of the patch preparation can be controlled by adjusting, for example, the thickness of the inorganic oxide layer, the thickness and material of the polyester base layer, and the thickness, material, and basis weight of the polyester nonwoven fabric layer, in the support. The moisture permeability can be measured in conformity with JIS L1099.

Practically, the pressure-sensitive adhesive surface of the pressure-sensitive adhesive layer can be covered with a release liner for protecting the surface before its use. The release liner is not particularly limited. Specific examples of the release liner include a glassine paper, a polyethylene, a polypropylene, a polyester, a polyethylene terephthalate, a polystyrene, an aluminum film, a polyethylene foam film, and a polypropylene foam film, and a laminated product thereof, a silicone-processed product thereof, and an emboss-processed product thereof. A release liner made of a polyester (especially polyethylene terephthalate) resin is preferred in terms of barrier property, a price, and the ease with which a material for the liner is selected. The surface on the pressure-sensitive adhesive layer side of the release liner may be subjected to a surface release treatment in order that the release liner can be released from the pressure-sensitive adhesive layer with additional ease.

The release liner preferably has a uniform thickness in consideration of the ease of processing and processing accuracy. The thickness of the release liner is preferably 25 μm to 200 μm, more preferably 50 μm to 150 μm from the viewpoints of, for example, the ease with which the patch preparation is produced, a cost for the release liner, and the portability and operability of the patch preparation.

The patch preparation of the present invention can be produced by any appropriate method. For example, the following method is given. First, the support is produced. Specifically, the inorganic oxide is deposited from the vapor onto the surface of the polyester film. Thus, a laminate of the polyester base layer and the inorganic oxide layer is obtained. Next, the polyester nonwoven fabric is laminated on the inorganic oxide layer of the laminate. Thus, the support is obtained. The lamination of the polyester nonwoven fabric can be performed by, for example, applying any appropriate adhesive to the inorganic oxide layer side of the laminate with a gravure coater or the like so that a dry application amount may be about 1 to 3 g/m$^2$, and crimping the nonwoven fabric while performing heating as required. A known adhesive such as a polyester-based, acrylic, vinyl chloride-based, vinyl acetate-based, rubber-based, or urethane-based adhesive can be used as the adhesive. Next, the release liner is prepared, the pressure-sensitive adhesive layer is laminated on one surface of the release liner, and the support is laminated on the pressure-sensitive adhesive layer. Thus, a laminated sheet is obtained. Alternatively, the laminated sheet is obtained by: laminating the pressure-sensitive adhesive layer on the polyester base layer of the support; and laminating the release liner on the pressure-sensitive adhesive layer. An approach to laminating the support and the pressure-sensitive adhesive layer is not particularly limited. Specific examples thereof include application, bonding, fusion, and welding. The following method is preferably adopted. A pressure-sensitive adhesive containing, for example, the drug, the adherent polymer, and an organic solvent is prepared, and then the pressure-sensitive adhesive is applied onto the release liner or the support, followed by the drying and removal of the organic solvent. The resultant laminated sheet is cut into a predetermined shape. Thus, the patch preparation is obtained. The patch preparation can be packaged in any appropriate packaging container as desired. A bag or the like made of a resin film, a metal foil, or a laminated film thereof is typically used as the packaging container.

Hereinafter, the present invention is described in more detail by way of examples. However, the present invention is not limited to these examples. It should be noted that the terms "part(s)" and "%" in the examples refer to "part(s) by weight" and "wt %," respectively unless otherwise stated.

<Preparation of Support>

Support A: A polyethylene terephthalate (PET) film having a thickness of 4 μm was used.

Support B: Aluminum oxide was deposited from the vapor onto one surface of the support A so as to have a thickness of 10 nm.

Support C: A PET nonwoven fabric (having a weight per unit area of 12 g/m$^2$) was attached to the deposited surface of the support B.

Support D: A PET nonwoven fabric (having a weight per unit area of 12 g/m$^2$) was attached to one surface of the support A.

Support E: A PET nonwoven fabric (having a weight per unit area of 12 g/m$^2$) was attached to one surface of a PET film having a thickness of 12 μm.

Support F: A PET nonwoven fabric (having a weight per unit area of 12 g/m$^2$) was attached to one surface of a PET film having a thickness of 25 μm.

(Preliminary Test)

The supports D, E, and F were subjected to Evaluations a. and b. below. Table 1 below shows the results.

a. Moisture Permeability

The moisture permeability of each of the supports D, E, and F was measured with a moisture-permeable cup described in JIS L1099 "method of testing a fiber product for its moisture permeability" in conformity with the standard by the following procedures.

(1) About 25 g of calcium chloride were weighed in the moisture-permeable cup.

(2) The support cut into a circular shape having a diameter of 70 mm was mounted so as to be concentric with the cup.

(3) A test body was obtained by: sequentially mounting a packing made of a synthetic resin and a metal ring on the moisture-permeable cup; fixing a side surface after the mounting with a wing nut; and sealing the side surface with a vinyl pressure-sensitive adhesive tape.

(4) The test body was placed in a thermo-hygrostat with its temperature and relative humidity kept at 40±2° C. and 90±5%, respectively.

(5) After a lapse of 16 hours or more, the test body was taken out of the thermo-hygrostat and then its temperature was equilibrated with room temperature. After that, its weight was measured. The weight was defined as an initial weight (hereinafter described as "initial").

(6) The test body was placed again in the thermo-hygrostat with its temperature and relative humidity kept at 40±2° C. and 90±5%, respectively.

(7) After 24 hours from the procedure (6), the test body was taken out of the thermo-hygrostat and then its temperature was equilibrated with room temperature. After that, its weight was measured. The weight was defined as a weight after 24 hours (hereinafter described as "24 hours").

(8) The test body was placed again in the thermo-hygrostat with its temperature and relative humidity kept at 40±2° C. and 90±5%, respectively.

(9) After 24 hours from the procedure (8), the test body was taken out of the thermo-hygrostat and then its temperature was equilibrated with room temperature. After that, its weight was measured. The weight was defined as a weight after 48 hours (hereinafter described as "48 hours").

(10) A value obtained by rounding a value calculated for each test body from the following equation to an integer value was defined as its moisture permeability.

Moisture permeability$(g/m^2 \cdot 24\ h) = (240 \times m)/(t \times s)$ s: A moisture permeation area $(cm^2) = 28.26$ t: The total time (h) of two weighing intervals$=48$ m: A total mass increase (mg) during the two weighing intervals The moisture permeation area s is a value calculated from the inner diameter of the moisture-permeable cup, i.e., 3.0 (cm) with a circle ratio of 3.14. In addition, the term "weighing interval" refers to an interval from "initial" to "24 hours" or from "24 hours" to "48 hours," and m can be represented as described below.

$m$=("24 Hours"−"initial")+("48 hours"−"24 hours")
 ="48 hours"−"initial"

Table 1 below shows the resultant moisture permeabilities.

b. Softness

The supports D, E, and F were each subjected to a softness measurement experiment in accordance with a heart loop method specified in JIS L1096 by the following procedures. Table 1 below shows the results. It should be noted that a smaller value for the softness in the heart loop method generally means that a sample is harder and a larger value therefor generally means that the sample is softer.

(1) Each support was cut into a size measuring 2 cm by 25 cm.

(2) The resultant test piece was formed into a heart loop so that its effective length was 20 cm and its nonwoven fabric surface faced inward. Both of its ends were fixed with a pressure-sensitive adhesive tape and then the loop was horizontally held in a state where the fixed point was placed upward.

(3) After a lapse of 1 minute, a distance L (mm) between the apex portion (fixed point) and the lowest point of the loop was measured to a whole digit.

(4) The procedure (3) was performed in the same manner as in the procedure (2) except that the nonwoven fabric surface was caused to face outward in the procedure (2).

(5) An average was calculated from the values obtained in the procedures (3) and (4), and was defined as the softness of the support.

Reference Example 1

Under an inert gas atmosphere, 95 parts of 2-ethylhexyl acrylate, 5 parts of acrylic acid, and 0.2 part of benzoyl peroxide as a polymerization initiator were compounded in ethyl acetate, and were then subjected to solution polymerization. Thus, a solution of an acrylic polymer A having a weight-average molecular weight of about 1,500,000 was obtained. An ethyl acetate solution containing 43 parts of the acrylic polymer A as a solid content, 17 parts of isosorbide dinitrate (ISDN), and 40 parts of isopropyl myristate as an organic liquid component were mixed. The mixed liquid was applied onto a PET film having a thickness of 75 μm as a release liner so that its thickness after drying was 40 μm, followed by drying in a circulating hot air dryer at 80° C. for 5 minutes. Thus, a pressure-sensitive adhesive layer was obtained. The pressure-sensitive adhesive layer was attached to the PET film surface of the support D. Thus, a patch preparation was obtained. The resultant patch preparation was subjected to Evaluations c. and d. below. Table 1 below shows the results.

Reference Example 2

A patch preparation was obtained in the same manner as in Reference Example 1 except that the support E was used instead of the support D. The resultant patch preparation was subjected to Evaluations c. and d. below. Table 1 below shows the results.

Reference Example 3

A patch preparation was obtained in the same manner as in Reference Example 1 except that the support F was used instead of the support D. The resultant patch preparation was subjected to Evaluations c. and d. below. Table 1 below shows the results.

c. Hairless Mouse Skin Permeability Test (1) The patch preparations of Reference Examples 1 to 3 each cut into a circular shape having a diameter of 8 mm were each released from the release liner and then attached to the keratin surface of a skin extirpated from a hairless mouse that had been stamped into a circular shape having a diameter of 20 mm.

(2) The skin prepared in the procedure (1) was mounted on a flow-through-type diffusion cell so that the back surface of the surface to which the preparation had been attached contacted a receptor liquid. It should be noted that a physiological saline solution at 32° C. was used as the receptor liquid.

(3) The receptor liquid was sampled every three hours, a drug concentration in the sampled liquid was determined by an HPLC method, and a cumulative permeation amount (μg/$cm^2 \cdot 12$ h) up to a lapse of 12 hours was determined.

Further, an evaluation for drug permeability was performed by the following criteria.
(Criteria)
  ○: The cumulative permeation amount is larger than that of Reference Example 1.
  x: The cumulative permeation amount is smaller than that of Reference Example 1.

Table 1 below shows the cumulative permeation amounts and the results of the evaluation for drug permeability.

d. Evaluation for Patch Feeling

The patch preparations of Reference Examples 1 to 3 each stamped into a size measuring 5 cm by 5 cm were each evaluated for its patch feeling when released from the release liner and attached to a skin by the following criteria on the assumption that the patch preparation was actually applied. Table 1 below shows the results.
(Criteria)
  ○: There is no stiff feeling (uncomfortable feeling).
  Δ: There is a weak stiff feeling (uncomfortable feeling).
  x: There is a strong stiff feeling (uncomfortable feeling).

TABLE 1

| | | Reference Example 1 | Reference Example 2 | Reference Example 3 |
|---|---|---|---|---|
| Support | Kind | D | E | F |
| | Base layer | 4 μm | 12 μm | 25 μm |
| | Inorganic oxide layer | — | — | — |
| | Nonwoven fabric layer | Present | Present | Present |
| | Moisture permeability ($g/m^2 \cdot 24$ h) | 152 | 55 | 33 |
| | Softness (mm) | 57 | 46 | 41 |
| Patch preparation | Cumulative drug permeation amount ($\mu g/cm^2 \cdot 12$ h) | 193 | 321 | 332 |
| | Drug permeability | Reference | ○ | ○ |
| | Patch feeling | ○ | Δ | x |

As is apparent from Table 1, the moisture permeability of a support reduces and its softness also reduces as the base layer of the support becomes thicker. In addition, the patch preparations of Reference Example 2 and Reference Example 3 have clearly larger cumulative drug permeation amounts than that of the patch preparation of Reference Example 1. This shows that the use of a support having a low moisture permeability caused a high ODT effect. On the other hand, with regard to a patch feeling, the patch preparation of Reference Example 1 was most excellent, the patch preparation of Reference Example 2 provided a slight uncomfortable feeling, though the feeling fell within an allowable range, and the patch preparation of Reference Example 3 provided a strong uncomfortable feeling. This shows that the flexibility of a patch preparation is insufficient when its support has a low softness (that is, the support is hard). The foregoing results have revealed that the moisture permeability can be reduced by increasing the thickness of the base layer of a support, and as a result, the drug permeability of a patch preparation can be improved, but in such case, its flexibility reduces and hence it becomes difficult to achieve compatibility with its patch feeling.

Example 1

Under an inert gas atmosphere, 95 parts of 2-ethylhexyl acrylate, 5 parts of acrylic acid, and 0.2 part of benzoyl peroxide as a polymerization initiator were compounded in ethyl acetate, and were then subjected to solution polymerization. Thus, a solution of an acrylic polymer A having a weight-average molecular weight of about 1,500,000 was obtained. An ethyl acetate solution containing 43 parts of the acrylic polymer A as a solid content, 17 parts of isosorbide dinitrate (ISDN), 40 parts of isopropyl myristate as an organic liquid component, and 0.07525 part of an isocyanate-based cross-linking agent were mixed. The mixed liquid was applied onto a PET film having a thickness of 75 μm as a release liner so that its thickness after drying was 60 μm, followed by drying in a circulating hot air dryer at 80° C. for 5 minutes. Thus, a pressure-sensitive adhesive layer was obtained. The pressure-sensitive adhesive layer was attached to the PET film surface of the support C. Thus, a patch preparation was obtained. The resultant patch preparation was subjected to Evaluations 1. to 6. below. Table 2 below shows the results.

Comparative Example 1

A patch preparation was obtained in the same manner as in Example 1 except that: the support B was used instead of the support C; and the pressure-sensitive adhesive layer was laminated on the aluminum oxide-deposited surface. The resultant patch preparation was subjected to Evaluations 1. to 6. below. Table 2 below shows the results.

Comparative Example 2

A patch preparation was obtained in the same manner as in Example 1 except that: the support D was used instead of the support C; and the pressure-sensitive adhesive layer was attached to the nonwoven fabric surface. The resultant patch preparation was subjected to Evaluations 1. to 4. and 6. below. Table 2 below shows the results.

Comparative Example 3

A patch preparation was obtained in the same manner as in Example 1 except that the pressure-sensitive adhesive layer was attached to the nonwoven fabric surface of the support C. The resultant patch preparation was subjected to Evaluations 1. to 6. below. Table 2 below shows the results.

1. Moisture Permeability

Moisture permeability measurement was performed by the same method as the method for Evaluation a. above except that each of the patch preparations of Example 1, and Comparative Examples 1 to 3 was used as an object instead of a support. At that time, the test was performed after the release liner was removed. Table 2 below shows the results.

2. Softness

Softness measurement was performed by the same method as the method for Evaluation b. above except the following. Each of the patch preparations of Example 1, and Comparative Examples 1 to 3 was used as an object, a test piece was obtained by cutting the patch preparation into a size measuring 1 cm by 15 cm, and a heart loop was formed so that its effective length was 13 cm and the pressure-sensitive adhesive layer faced inward. Table 2 below shows the results.

3. Hairless Mouse Skin Permeability Test

A hairless mouse skin permeability test was performed with each of the patch preparations of Example 1, and Comparative Examples 1 to 3 as an object in the method for Evaluation c. above to determine a cumulative permeation amount (μg/cm²·12 h) up to a lapse of 12 hours.

Further, an evaluation for drug permeability was performed by the following criteria.

(Criteria)

○: The cumulative permeation amount is larger than that of Comparative Example 2.

x: The cumulative permeation amount is smaller than that of Comparative Example 2.

Table 2 below shows the cumulative permeation amounts and the results of the evaluation for drug permeability.

4. Evaluation for Handleability

The patch preparations of Example 1, and Comparative Examples 1 to 3 each stamped into a size measuring 5 cm by 5 cm were each evaluated for its handleability when released from the release liner and attached to a skin by the following criteria on the assumption that the patch preparation was actually applied. Table 2 below shows the results.

(Criteria)

○: It is easy to attach the patch preparation to the skin without causing any wrinkle.

x: It is difficult to attach the patch preparation to the skin without causing any wrinkle.

5. Evaluation for Durability of Inorganic Oxide Layer

Each of the patch preparations of Example 1, and Comparative Examples 1 and 3 each using a support having an inorganic oxide layer was rubbed by the following procedures, and then its moisture permeability was measured in the same manner as in Evaluation a. above.

(1) An area measuring 4.5 cm long by 4.5 cm wide was punched out and removed from the central portion of a PET film which had a thickness of 75 μm, and measured 10 cm long by 10 cm wide, and one surface of which had been subjected to a release treatment.

(2) A test body was obtained by attaching the pressure-sensitive adhesive layer of the patch preparation released from the liner to the surface of the PET film subjected to the release treatment so that the patch preparation covered the entirety of the portion from which the PET film had been removed.

(3) A portion of the test body where the PET film and the patch preparation were attached to each other was held by being sandwiched between fingers, a metal bar having a diameter of 1 cm was pressed against the support surface of the preparation, and the surface was rubbed with the metal bar at a rate of one reciprocation per second 40 times in a state where the test body was bent.

An evaluation for durability was performed with the moisture permeability measured after the rubbing by the following evaluation criteria.

(Criteria)

○: The moisture permeability after the rubbing is smaller than the moisture permeability of Comparative Example 2.

x: The moisture permeability after the rubbing is larger than the moisture permeability of Comparative Example 2.

Table 2 below shows the moisture permeabilities after the rubbing and the results of the evaluation for the durability of the inorganic oxide layer.

6. Evaluation for External Appearance (Texture and Conspicuity)

On the assumption that the patch preparations of Example 1 and Comparative Examples 1 to 3 were actually applied, the patch preparations, each of which had been stamped into a size measuring 5 cm by 5 cm, were each attached to a skin, and then evaluated for its texture and conspicuity under ambient light by the following criteria. Table 2 below shows the results.

(Criteria)

○: The ambient light is diffused and reflected, and hence the patch preparation shows a texture with a mat feeling and is inconspicuous.

x: The ambient light undergoes mirror reflection, and hence the patch preparation shows a texture with a glaring feeling and is conspicuous.

TABLE 2

|  | Example 1 | Comparative Example 1 | Comparative Example 2 | Comparative Example 3 |
|---|---|---|---|---|
| Support | C | B | D | C |
| Base layer | 4 μm | 4 μm | 4 μm | 4 μm |
| Inorganic oxide layer | $Al_2O_3$ | $Al_2O_3$ | — | $Al_2O_3$ |
| Nonwoven fabric layer | Present | — | Present | Present |
| Surface bonding to pressure-sensitive adhesive layer | Base layer | Inorganic oxide layer | Nonwoven fabric layer | Nonwoven fabric layer |
| Moisture permeability (g/m² · 24 h) | 7 | 47 | 92 | 20 |
| Cumulative drug permeation amount (μg/cm² · 12 h) | 392 | 298 | 264 | 304 |
| Drug permeability | ○ | ○ | Reference | ○ |
| Softness (mm) | 47 | 62 | 47 | 47 |
| Handleability | ○ | x | ○ | ○ |
| Moisture permeability after rubbing (g/m² · 24 h) | 26 | 123 | — | 58 |
| Durability of inorganic oxide layer | ○ | x | — | ○ |
| External appearance | ○ | x | x | x |

As is apparent from Table 2, each of the patch preparations of Example 1, and Comparative Example 1 and Comparative Example 3, each using a support having an inorganic oxide layer, shows a lower moisture permeability and higher drug permeability than that of the patch preparation of Comparative Example 2 using a support free of any inorganic oxide layer. Further, as a result of the combined use of the inorganic oxide layer and the nonwoven fabric layer, the extent to which the moisture permeability of each of the patch preparations of Example 1 and Comparative Example 3 reduces is markedly large as compared with Comparative Example 1 using the inorganic oxide layer alone and Comparative Example 2 using the nonwoven fabric layer alone. This suggests that the combined use of the inorganic oxide layer and the nonwoven fabric layer can exert a synergistic effect. Further, surprisingly, the moisture permeability of the patch preparation of Example 1 is additionally reduced as compared with that of Comparative Example 3, in which the pressure-sensitive adhesive layer is attached to the nonwoven fabric layer of the support, by attaching the pressure-sensitive adhesive layer to the base layer of the support. Although a mechanism for the phenomenon was unknown, the adhesion of the pressure-sensitive adhesive layer and the base layer as a PET film was assumed to exert an effect. In addition, each of the patch preparations of Example 1, and Comparative Example 2 and Comparative Example 3 each using a support having a nonwoven fabric layer has moderate flexibility and shows excellent handleability. On the other hand, the softness of the patch preparation of Comparative Example 1 was high. In other words, the flexibility of the patch preparation was so high that it was difficult to attach the patch preparation. Further, with regard to the durability of the inorganic oxide layer, the extent to which the moisture permeability of each of the patch preparations of Example 1 and Comparative Example 3 increases after the rubbing is markedly small as compared with that of the patch preparation of Comparative Example 1. Accordingly, it is found that providing the base layer and the nonwoven fabric layer improves the durability of the inorganic oxide layer. Further, the patch preparation of Example 1 showed a texture with a mat feeling and had an inconspicuous external appearance because the nonwoven fabric layer as the exposed surface of the support diffused and reflected the ambient light.

As described above, the patch preparation according to the example of the present invention is reduced in moisture permeability to effectively improve the releasability of the drug. In addition, the patch preparation can improve the durability of the inorganic oxide layer, and can realize excellent handleability, patch feeling, and external appearance.

The patch preparation of the present invention can be suitably utilized in, for example, the transdermal administration of a drug.

Many other modifications will be apparent to and be readily practiced by those skilled in the art without departing from the scope and spirit of the invention. It should therefore be understood that the scope of the appended claims is not intended to be limited by the details of the description but should rather be broadly construed.

What is claimed is:

1. A patch preparation, comprising:
    a support; and
    a pressure-sensitive adhesive layer containing an adherent polymer and a drug on one surface of the support,
    wherein:
    the support has a polyester base layer, an inorganic oxide layer, and a polyester nonwoven fabric layer in the stated order;
    the polyester base layer has a thickness of 1.0 μm to 16 μm; and
    the pressure-sensitive adhesive layer is laminated on the polyester base layer.

2. A patch preparation according to claim 1, wherein the inorganic oxide layer has a thickness of 1 nm to 300 nm.

3. A patch preparation according to claim 1, wherein the patch preparation has a moisture permeability of 0.1 g/m²·24 h to 80 g/m²·24 h.

4. A patch preparation according to claim 1, wherein the adherent polymer comprises an acrylic polymer obtained by copolymerizing a (meth)acrylic acid alkyl ester and a functional monomer.

5. A patch preparation according to claim 1, wherein the pressure-sensitive adhesive layer has a thickness of 10 μm to 200 μm.

6. A patch preparation according to claim 1, wherein the pressure-sensitive adhesive layer further contains an organic liquid component.

* * * * *